US008802446B2

(12) United States Patent
Nakayama et al.

(10) Patent No.: US 8,802,446 B2
(45) Date of Patent: Aug. 12, 2014

(54) METHOD FOR MEASURING CYSTATIN C IN HUMAN BODY FLUID

(75) Inventors: Shinya Nakayama, Ryugasaki (JP);
Hiroshi Takahashi, Ryugasaki (JP);
Yasushi Nakamura, Ryugasaki (JP);
Tomo Shimizu, Ryugasaki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 0 days.

(21) Appl. No.: 13/132,790

(22) PCT Filed: Dec. 3, 2009

(86) PCT No.: PCT/JP2009/006590
§ 371 (c)(1),
(2), (4) Date: Jun. 3, 2011

(87) PCT Pub. No.: WO2010/064435
PCT Pub. Date: Jun. 10, 2010

(65) Prior Publication Data
US 2011/0236996 A1    Sep. 29, 2011

(30) Foreign Application Priority Data

Dec. 4, 2008    (JP) ................................. 2008-309369

(51) Int. Cl.
*G01N 33/543*    (2006.01)

(52) U.S. Cl.
CPC .................................... *G01N 33/543* (2013.01)
USPC ............ 436/518; 435/7.1; 435/7.92; 436/523

(58) Field of Classification Search
None
See application file for complete search history.

(56) References Cited

U.S. PATENT DOCUMENTS

| 6,248,597 B1 | 6/2001 | Eda et al. |
| 2003/0219910 A1 | 11/2003 | Yugawa et al. |
| 2008/0044926 A1 | 2/2008 | Honjo et al. |
| 2008/0075419 A1 | 3/2008 | Okubo et al. |
| 2009/0263915 A1 | 10/2009 | Yoshida et al. |
| 2010/0047922 A1 | 2/2010 | Sunde et al. |

FOREIGN PATENT DOCUMENTS

| CN | 1459634 | 12/2003 |
| CN | 101088010 | 12/2007 |
| CN | 101356438 A | 1/2009 |
| CN | 101377492 A | 3/2009 |
| JP | 11 108929 | 4/1999 |
| WO | WO 2006/028132 A1 | 3/2006 |
| WO | 2007 102054 | 9/2007 |
| WO | WO 2008/012944 | 1/2008 |
| WO | WO 2008/142057 A1 | 11/2008 |

OTHER PUBLICATIONS

Stowe et al., Analytical Performance of a Particle-enhanced Nephelometric Immunoassay for Serum Cystatin C Using Rate Analysis, Clinical Chemistry 47(8): 1482-1485, 2001.*
Ishiguro, Hiroshi; et al. "The Use of Monoclonal Antibodies to Define Levels of Cystatin C in Normal Human Serum." Hybridoma, vol. 8, No. 3. pp. 303-313 (1989).
Olafsson, Isleifur; et al. "Production, characterization and use of monoclonal antibodies against the major extracellular human cysteine proteinase inhibitors cystatin C and kininogen." Scand J Clin Lab Invest, vol. 48, No. 6. pp. 573-582 (1988).
Kyhse-Andersen, Jan; et al. "Serum Cystatin C, Determined by a Rapid, Automated Particle-Enhanced Turbidimetric Method, Is a Better Marker than Serum Creatinine for Glomerular Filtration Rate." Clinical Chemistry, vol. 40, No. 10. pp. 1921-1926 (1994).
Newman, David; et al. "Serum cystatin C measured by automated immunoassay: A more sensitive marker of changes in GFR than serum creatinine." Kidney International, vol. 47. pp. 312-318 (1995).
Finney, Hazel; et al. "Initial evaluation of cystatin C measurement by particle-enhanced immunonephelometry on the Behring nephelometer systems (BNA, BNII)." Clinical Chemistry, vol. 43, No. 6. pp. 1016-1022 (1997).
Abrahamson, Magnus. "Cystatins." Methods in Enzymology, vol. 244. pp. 685-700 (1994).
International Search Report and Written Opinion issued Jan. 26, 2010 in PCT/JP09/06590 filed Dec. 3, 2009.
Extended European Search Report issued Mar. 23, 2012 in patent application No. 09830205.2, Mar. 23, 2012.
Lars-Olof Hansson, et al., "Comparison between Chicken and Rabbit Antibody Based Particle Enhanced Cystatin C Reagents for Immunoturbidimetry", Journal of Immunoassay and Immunochemistry, vol. 29, No. 1, XP008093538, Jan. 1, 2008, pp. 1-9.

* cited by examiner

*Primary Examiner* — Gary W Counts
(74) *Attorney, Agent, or Firm* — Oblon, Spivak, McClelland, Maier & Neustadt, L.L.P.

(57) ABSTRACT

Provided is a method and reagent for measuring cystatin C in a human body fluid, by contacting a human body fluid with (a) first insoluble carrier particles coated with a first anti-human cystatin C monoclonal antibody and (b) second insoluble carrier particles coated with a second anti-human cystatin C monoclonal antibody, where the first anti-human cystatin C monoclonal antibody has an affinity for cystatin C that is higher than the second anti-human cystatin C monoclonal antibody, the second anti-human cystatin C monoclonal antibody recognizes an epitope of cystatin C that is different from the epitope recognized by the first anti-human cystatin C monoclonal antibody, and the first and second insoluble carrier particles are coated with from 1% to less than 4% by weight of the anti-human cystatin C monoclonal antibodies.

14 Claims, 4 Drawing Sheets

METHOD FOR MEASURING CYSTATIN C IN HUMAN BODY FLUID

TECHNICAL FIELD

The present invention relates to a particle-enhanced immunoassay method for cystatin C in a human body fluid, and a particle-enhanced immunoassay reagent.

BACKGROUND ART

Cystatin C is a basic low molecular weight protein (isoelectric point pH 9.3) having a molecular weight of 13 kDa, and is continually produced in all of nucleated cells in the human body, while a certain amount is secreted extracellularly without being affected by environmental changes. Therefore, the concentration of cystatin C in blood becomes constant, and is not subject to the influence such as inflammation due to other diseases, or to the influence of age, gender, exercise, meal or the like. Furthermore, cystatin C does not form composites with other plasma proteins, but is filtered at the renal glomerulus and reabsorbed in the proximal renal tubule. Therefore, it is known that if the glomerular filtration rate (GFR) decreases, the blood concentration of cystatin C increases, and accordingly, cystatin C is attracting attention as an indicator of the GFR instead of creatinine. Furthermore, since cystatin C serves as a diagnostic indicator of early renal failure in test for renal function, cystatin C is widely useful also in the areas of ambulatory care, medical examination and the like.

In regard to the method for measuring cystatin C, there have been reported automated particle-enhanced immunoassay methods for human cystatin C (Non-Patent Documents 1 to 3, and Patent Document 1). For example, in the method described in Non-Patent Document 1, use is made of an anti-cystatin C polyclonal antibody having a strong agglutinating power, which is in the form of being bound to carrier particles at a weight ratio of 5%. However, as shown in Non-Patent Document 4, cystatin C belongs to the cystatin family in which the members are similar in structure, and cystatin C is differently localized in various types of human body fluids. Accordingly, there is a very high possibility that an accurate measurement value for cystatin C may not be obtained with a polyclonal antibody which has low specificity, depending on the type of the human body fluid (for example, saliva or lacrimal fluid). Meanwhile, Patent Document 1 describes information to the effect that generally an immunoagglutinate is more easily formed when a polyclonal antibody is used (page 20, lines 21 to 27). Furthermore, it is suggested to use an anti-cystatin C monoclonal antibody having high specificity. However, it is also described to the effect that in the case the target is a monomer and low molecular weight proteins such as cystatin C, better results are obtained by using a cocktail of many different monoclonal antibodies (page 21, lines 5 to 10), which is essentially equivalent to the use of a polyclonal antibody. Moreover, in order to improve the performance, it has been necessary to bind a markedly large amount of antibodies such that the binding amount of antibodies to the total weight of antibody-coated particles is greater than 5% by weight and equal to or less than 35% by weight.

PRIOR ART DOCUMENTS

Patent Documents

Patent Document 1: WO 2007/102054 Pamphlet

Non-Patent Documents

Non-Patent Document 1: CLINICAL CHEMISTRY, Vol. 40, No. 10 (1994), 1921-1926
Non-Patent Document 2: KIDNEY INTERNATIONAL, Vol. 47 (1995), 312-318
Non-Patent Document 3: CLINICAL CHEMISTRY, Vol. 43, No. 6 (1997), 1016-1022
Non-Patent Document 4: METHODS IN ENZYMOLOGY, Vol. 244 (1994), 685-700

DISCLOSURE OF INVENTION

Problem to be Solved by the Invention

There has been a problem that polyclonal antibodies that are generally used in the particle-enhanced immunoassay methods for human cystatin C have low specificity, and an assay that is specific to cystatin C cannot be carried out depending on the type of sample. As a measure against the problem, it has been designed to use monoclonal antibodies; however, since their agglutinating power is weak, it is necessary to bind a large amount of cocktail composed of multiple types of monoclonal antibodies to insoluble carrier particles, posing a new problem that enormous efforts and costs are required. Therefore, the particle-enhanced immunoassay methods for cystatin C in a human body fluid which involve monoclonal antibodies only, have not been hitherto put to practical use. In addition, the conventional particle-enhanced immunoassay methods for human cystatin C require large amounts of antibodies such that the binding amount relative to the total weight of antibody-coated particles is greater than 5% by weight and equal to or less than 35% by weight, in order to obtain practical performance.

Therefore, it is an object of the present invention to provide a particle-enhanced immunoassay method for cystatin C in a human body fluid, which has high specificity and can be easily automated at low cost.

Means for Solving Problem

The inventors of the present invention conducted a thorough investigation in order to solve the problems described above, and as a result, they found that even for monoclonal antibodies that have been conventionally regarded inappropriate for cystatin C assays, when antibody-coated particles are combined in which an anti-human cystatin C monoclonal antibody having high affinity and an anti-human cystatin C monoclonal antibody recognizing an epitope different from that of the aforementioned monoclonal antibody and having relatively low affinity are each independently bound to the antibody-coated particles at a binding amount ratio of less than 5% by weight relative to the total weight of the antibody-coated particles, a cystatin C-specific particle-enhanced immunoassay can be achieved. Thus, the inventors completed the present invention.

That is, the present invention is to provide a method for measuring cystatin C in a human body fluid, the method being a particle-enhanced immunoassay method comprising a combination of antibody-coated particles in which some insoluble carrier particles are coated with anti-human cystatin C monoclonal antibodies of one type which have high affinity, and in which some other insoluble carrier particles are coated with anti-human cystatin C monoclonal antibodies of another type which recognize an epitope different from that the monoclonal antibodies of the first-mentioned type and have relatively low affinity, wherein the binding amount of anti-human cystatin C monoclonal antibodies of either type relative to the total weight of the particles being coated with the corresponding antibodies is less than 5% by weight.

Furthermore, the present invention is to provide a particle-enhanced immunoassay reagent specific to cystatin C in a human body fluid, the reagent comprising being a combination of antibody-coated particles in which some insoluble carrier particles are coated with anti-human cystatin C monoclonal antibodies of one type having high affinity and, in which some other insoluble carrier particles are coated with anti-human cystatin C monoclonal antibodies of another type which recognize an epitope different from that the monoclonal antibodies of the first-mentioned type recognize and have relatively low affinity, wherein the binding amount of anti-human cystatin C monoclonal antibodies of either type relative to the total weight of the particles being coated with the corresponding antibodies is less than 5% by weight.

Effect of the Invention

According to the present invention, it has been made possible to provide a particle-enhanced immunoassay and reagent for cystatin C in a human body fluid, which have higher specificity than the conventional methods and reagents, and can be easily applied to automatic analyzers at low cost.

BEST MODE(S) FOR CARRYING OUT THE INVENTION

Figure 1:
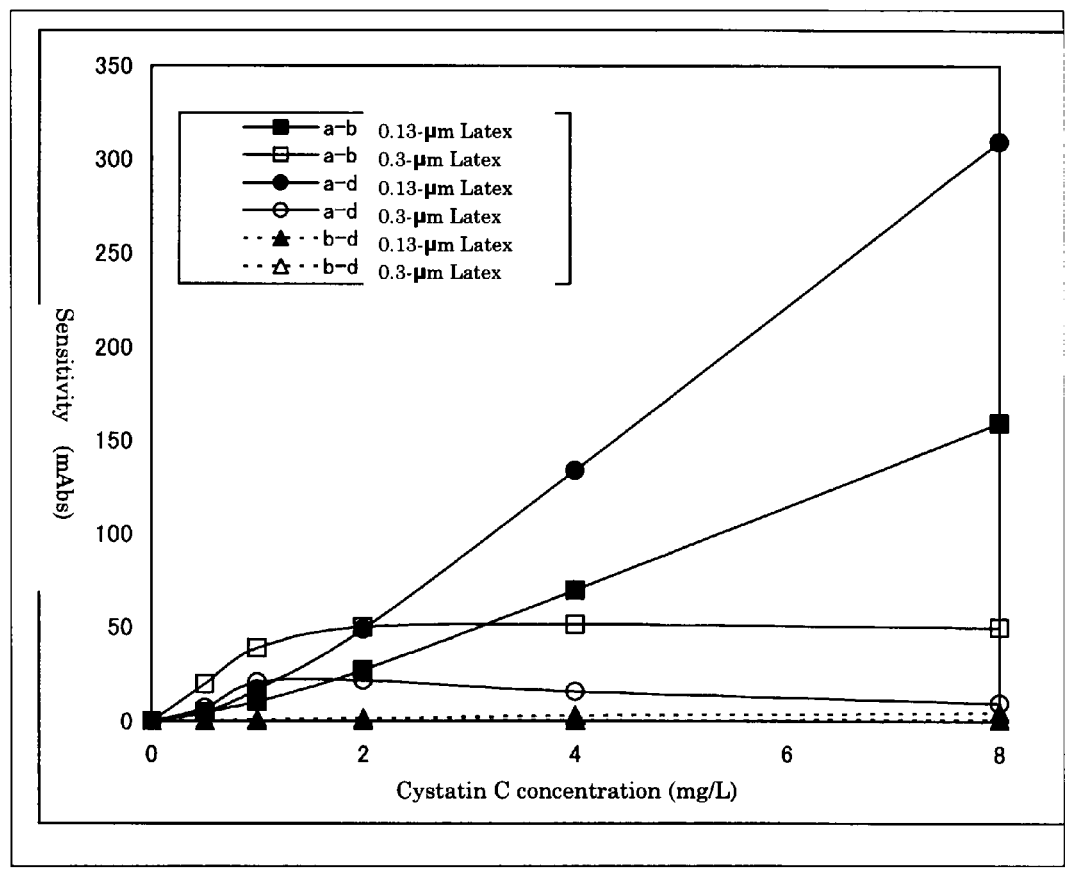
FIG. 1 is a cystatin C concentration-sensitivity curve showing the sensitivity that accompanies particle-enhanced immunoagglutination when antibody-coated latex particles in which anti-human cystatin C monoclonal antibodies a, b and d were bound respectively to latex particles having particle sizes of 0.13 μm and 0.30 μm, were combined in the manner of a-b, a-d or b-d and with the same particle size, and cystatin C was measured.

Two or more kinds of anti-human cystatin C monoclonal antibodies, which specifically react with human cystatin C, are used in the present invention, and they shall include at least one from each kind of the following monoclonal antibodies: one has high affinity, and the other recognizes a different epitope and has relatively low affinity. The aforementioned antibodies also include an antibody fragment containing a functional site (that is, an antibody fragment containing Fab which is a human cystatin C recognition site) or a recombinant type antibody (that is, a recombinant antibody having a structure recombined at sites other than Fab).

There are no particular limitations on the method of obtaining the monoclonal antibody having high affinity as described above, but effective methods for obtaining an antibody having high affinity include selection of an immunization site or a hybridoma, an increase in the quantity of human cystatin C for immunization, prolongation of the immunization period, and the like. Here, the phrase "specifically react with human cystatin C" implies that the antibody causes an antigen-antibody reaction with human cystatin C, but substantially does not cause any antigen-antibody reaction with other cystatin family members (for example, human cystatin A, cystatin B, cystatin D, cystatin E/M, cystatin F, cystatin S, cystatin SA, and kininogen).

Among the anti-human cystatin C monoclonal antibodies used in the present invention, the anti-human cystatin C monoclonal antibody having high affinity has a dissociation constant (kd value), which is calculated by titer determination using, for example, an apparatus of "trade name: BIACORE (registered trademark), manufactured by GE Healthcare Corp.", of less than 1 nM, and preferably 0.5 nM or less. In an analysis made by the BIACORE apparatus, the dissociation constant of a monoclonal antibody having ordinary affinity is 1 nM or greater. There are no particular limitations on the method of examining the dissociation constant as long as the method is a conventional method that is known in the pertinent art, but there is a possibility that the dissociation constant may slightly fluctuate depending on the principle of assay or assay conditions.

Examples of such a high-affinity monoclonal antibody include a monoclonal antibody produced by Hybridoma 75202 (FERM BP-11186), which will be described in the following Examples.

According to the present invention, if at least one of the high-affinity monoclonal antibody described above is used, the other anti-human cystatin C monoclonal antibody having relatively low affinity may have ordinary affinity. Among such combinations, a combination in which the ratio obtained by dividing the dissociation constant of the anti-human cystatin C monoclonal antibody having relatively low affinity by the dissociation constant of the other high-affinity monoclonal antibody is 2 or greater, is preferred. Such monoclonal antibodies can be produced according to conventional methods. In addition, when there is a difference of two or more times in the affinity (relative ratio of dissociation constants), a combination of high-affinity monoclonal antibodies each having a dissociation constant of less than 1 nM, can also be used.

The two or more kinds of monoclonal antibodies used in the present invention constitute a combination of monoclonal antibodies, in which the respective monoclonal antibodies recognize different sites of human cystatin C. The fact that the recognition sites are different can be identified by, for example, a sandwich ELISA.

In regard to the particle-enhanced immunoassay method and reagent of the present invention, there are no particular limitations on the material that is used as the insoluble carrier particles as long as the material can be used as a component for examination reagents, but specific examples include latexes, metal colloids, silica and carbon. The size of the insoluble carrier particles can be appropriately selected from 0.05 μm to 0.5 μm in accordance with the particle-enhanced immunoassay method of the present invention and the detection principle employed for the reagent. An average particle size used for the optical assays employed for an automatic analyzer is generally 0.1 μm to 0.4 μm, and preferably 0.1 to 0.2 μm. The average particle size of the insoluble carrier particles can be examined using a particle size distribution analyzer, an electron microscope or the like.

The combination of monoclonal antibodies of the present invention enables a human cystatin C assay even when the binding amount of each of the antibodies relative to the total weight of the antibody-coated particles is less than 5% by weight, and the amount of antibodies is preferably equal to or greater than 1% by weight and less than 4% by weight.

Coating of monoclonal antibodies on insoluble carrier particles (sensitization) can be carried out by, for example, a conventional method called a physical adsorption method or a chemical binding method.

The sample as the object of assay for the particle-enhanced immunoassay method, reagent and kit is not particularly limited as long as it is a human body fluid and contains human cystatin C, such as blood serum, blood plasma, synovial fluid, milk, saliva, cerebrospinal fluid, seminal plasma, amniotic fluid, urine, and lacrimal fluid.

The particle-enhanced immunoassay method, reagent and kit of the present invention can be applied to a turbidimetric method using general-purpose automatic analyzers manufactured by Hitachi, Ltd. as well as Toshiba Corp., JEOL, Ltd., Olympus Corp., and Sekisui Medical Co., Ltd., or using an exclusive automatic analyzer LPIA (registered trademark) (manufactured by Mitsubishi Kagaku Iatron, Inc.) which uses near-infrared region as the measurement wavelength, and to a nephelometric method using an apparatus for measuring the scattered light intensity (manufactured by Dade Behring, Inc.), and therefore, the method, reagent and kit can be easily automated.

The reagent for particle-enhanced immunoagglutination assay of the present invention may contain, in addition to the main component, for example, acetic acid, citric acid, phosphoric acid, Tris, glycine, boric acid, carbonic acid, and Good's buffer, or sodium salts, potassium salts and calcium salts of the acids, as components for buffering the ionic strength, osmotic pressure and the like of the sample. Furthermore, the reagent may also contain a polymer such as polyethylene glycol, polyvinylpyrrolidone, or a phospholipid polymer, as a component for enhancing immunological agglutination. The reagent may also contain a single kind or a combination of plural kinds of the components that are generally used for particle-enhanced immunoagglutination assays, such as proteins, amino acids, sugars, metal salts, surfactants, reducing substances or chaotropic substances, as a component that controls the formation of immunological agglutination. Furthermore, the reagent may also be prepared into a kit containing these components in combination.

The particle-enhanced immunoassay method for human cystatin C and the particle-enhanced immunoassay reagent and kit of the present invention can be applied to any use, as long as the use is intended for measuring human cystatin C in a sample specifically with high accuracy.

EXAMPLES

Hereinafter, an embodiment of the present invention will be described in detail by way of a Production Example, Evaluation Examples, and an Example, but the present invention is not intended to be limited thereto.

Production Example

Production of High-Affinity Anti-Human Cystatin C Monoclonal Antibody

100 µg of purified human cystatin C (SCIPAC, Ltd.) was used for a single immunization. The first immunization was carried out using 200 µL of an emulsion prepared by mixing equal amounts of human cystatin C and Freund's complete adjuvant, by injecting this to the abdominal cavities of BALB/c mice. For additional immunization, long-term immunization was carried out in which additional immunization was repeated 6 times at an interval of 2 weeks in order to acquire an antibody having high affinity, using 200 µL of an emulsion prepared in the same manner using Freund's incomplete adjuvant. The antibody titers in the blood collected from the orbital vein of the mice were measured by ELISA, and mice which gave high antibody titer were selected and supplied to cell fusion. After two weeks from the seventh immunization, a solution prepared by dissolving 100 µg of human cystatin C in 200 µL of physiological saline, was injected into the abdominal cavity of each mouse, and after three days, the spleen was enucleated. The spleen was dissociated in RPMI1640 medium, and then the resultant was centrifuged at 1500 rpm to collect spleen cells. These cells were washed three or more times with bovine fetal serum-free RPMI1640 medium, and then suspended in 2 mL of RPMI1640 medium containing 15% bovine fetal serum which was added to the cells to obtain a spleen cell suspension. The spleen cells and myeloma cells SP2/0-AG14 were mixed at a ratio of 6:1, and then the cells were subjected to cell fusion in the presence of 50% polyethylene glycol. Thus, a hybridoma (fused cell) was obtained. The cells were centrifuged at 1500 rpm, and the precipitation was collected and suspended in GKN solution (a solution obtained by dissolving 2 g of glucose, 0.4 g of potassium chloride, 8 g of sodium chloride, 1.41 g of disodium hydrogen phosphate, and 0.78 g of sodium dihydrogen phosphate dihydrate in purified water, and adjusting the volume to 1 liter). The precipitation was washed by centrifugation, and the precipitation was collected. This collected precipitation was suspended in 30 mL of RPMI1640 medium containing 15% bovine fetal serum, and the suspension was dispensed into three 96-well microplates in an amount of 100 µL per well, together with 200 µL per well of HAT medium containing thymic cells of a BALB/c mouse in an amount of $2.5 \times 10^6$ cells/mL as feeder cells. The hybridoma was cultured in an incubator containing 5% carbon dioxide at 37° C.

The presence of an anti-human cystatin C antibody in the culture supernatant was identified by ELISA in which human cystatin C was immobilized, and after 10 days, proliferation of the hybridoma was confirmed in all of the wells. Specifically, 100 µL of 10 mM phosphate buffer solution (pH 7.2; hereinafter, abbreviated as PBS) containing 10 µg/mL of human cystatin C and 150 mM sodium chloride was dispensed on the 96-well microplate where proliferation of the hybridoma had been confirmed. The microplate was left to stand overnight at 4° C. Subsequently, this 96-well microplate was washed three times with 300 µL of PBS containing 0.05% TWEEN Tween 20 and 1% bovine serum albumin (hereinafter, BSA), and then the culture supernatant of the respective wells was added to the microplate in an amount of 50 µL/well and was left to stand for one hour at room temperature. Thereafter, the plate was washed three times with a PBS containing 0.05% TWEEN 20, and then a peroxidase-labeled anti-mouse antibody (manufactured by Sekisui Medical Co., Ltd.) was added to the microplate in an amount of 50 µL/well and was left to stand for one hour at room temperature. Thereafter, the microplate was washed three times with a PBS containing 0.05% TWEEN 20, and then a citrate buffer solution (pH 5) containing 0.2% ortho-phenylenediamine and 0.02% hydrogen peroxide was added to the microplate in an amount of 50 µL/well. The microplate was left to stand for 15 minutes at room temperature, and then 4.5 N sulfuric acid was added thereto in an amount of 50 µL/well to stop the reaction. The absorbance of each well at a wavelength of 492 nm was measured, and the wells having high absorbance were selected as positive wells.

The cells were rendered monoclonal by limiting dilution method. That is, on a 96-well microplate to which thymus cells of a BALB/c mouse had been dispensed in an amount of $10^6$ cells per well as feeder cells, 0.1 mL of a solution obtained by diluting the hybridoma in the positive wells to a concentration of 10 cells/mL, was dispensed in an amount of 0.1 mL each. Regarding the medium, HT medium was used for the first time, while RPMI1640 medium containing 15% bovine fetal serum was used since the second time, and the cells were cultured for 10 days in an incubator containing 5% carbon dioxide at 37° C. The monoclonalization operation based on the selection of positive wells according to ELISA and on a limiting dilution method was repeated three times, and hybridomas producing anti-human cystatin C monoclonal antibody having high reactivity were obtained. About $10^5$ cells of each of the hybridomas were administered to the abdominal cavity of a mouse which had been pretreated with pristane, and the ascites fluids were respectively collected. Insoluble materials were removed by centrifugation from each of the ascites fluids thus collected, and an equal amount of saturated ammonium sulfate solution was added thereto. The resulting mixture was left to stand overnight while stirred, and a precipitation was collected by centrifugation. The collected precipitation was dissolved in a 20 mM Tris buffer solution (pH 8), and dialyzed into the same buffer solution. Each of the dialysis contents was separately adsorbed to a DEAE-Sepharose column which had been equilibrated with the same buffer solution, and then elution was performed at a concentration gradient of 0 to 300 mM of sodium chloride in the same buffer solution. Thus, various purified anti-human cystatin C monoclonal antibodies were obtained.

Evaluation Example 1

Selection of Anti-Human Cystatin C Monoclonal Antibodies Recognizing Different Epitopes An investigation was made on combinations of anti-human cystatin C monoclonal antibodies recognizing different epitopes, which had been produced using the reactivity in sandwich ELISA as an index. Specifically, various anti-human cystatin C monoclonal antibodies were immobilized on a plate by adding a PBS containing 1 μg/mL each of the antibodies in an amount of 50 μL/well and leaving the plate to stand for 2 hours at room temperature. Subsequently, the plate was washed three times with 300 μL of PBS containing 0.05% TWEEN 20, and a PBS containing 0.05% TWEEN 20 and 1% BSA was added to the plate in an amount of 300 μL/well. The plate was left to stand for one hour at room temperature. Thereafter, the plate was washed three times with a PBS containing 0.05% TWEEN 20, and then a PBS containing 10 ng/mL of human cystatin C was added to the plate in an amount of 50 μL/well. The plate was left to stand for one hour at room temperature to allow a reaction to occur, and the plate was washed three times with a PBS containing 0.05% TWEEN 20. Then, a PBS containing 1 μg/mL of each of the anti-human cystatin C monoclonal antibodies which had been biotinated for detection, was added to the plate in an amount of 50 μL/well, and the plate was left to stand for one hour at room temperature. The plate was washed three times with a PBS containing 0.05% TWEEN 20, and then a peroxidase-labeled streptavidin (ZYMED Laboratories, Inc.) which was diluted to 5000 times, was added to the plate in an amount of 50 μL/well. The plate was left to stand for one hour at room temperature. The plate was washed three times with a PBS containing 0.05% TWEEN 20, and then a citrate buffer solution (pH 5) containing 0.2% ortho-phenylenediamine and 0.02% hydrogen peroxide was added to the plate in an amount of 50 μL/well to allow a reaction for 15 minutes at room temperature. Then, 4.5 N sulfuric acid was added in an amount of 50 μL/well to the plate to stop the reaction, and the absorbance of each well at a wavelength of 492 nm was measured. The antibodies of the combinations which were found to have reactivity were considered the monoclonal antibodies recognizing different epitopes. As a result, it was confirmed that four kinds of anti-human cystatin C monoclonal antibodies a to d could be used to constitute combinations such as indicated in Table 1.

TABLE 1

|  |  | Immobilized antibody | | | |
|---|---|---|---|---|---|
|  |  | a | b | c | d |
| Biotinated antibody | a | — | ++ | − | + |
|  | b | ++ | — | − | ++ |
|  | c | + | − | — | + |
|  | d | ++ | ++ | − | — |

++: Strongly reactive
+: Reactive
−: Non-reactive

It was confirmed that the antibody a could be combined with any of the antibodies b to d. Furthermore, in regard to the antibody c, since this antibody is not affected by the antibody that is combined therewith and does not exhibit reactivity when in a state of being immobilized, it is thought that binding to an insoluble carrier, that is, use in a particle-enhanced immunoassay where immobilization is required, is impossible.

Evaluation Example 2

Identification of Particle-Enhanced Immunoagglutination in a Combination of Anti-Human Cystatin C Monoclonal Antibodies Recognizing Different Epitopes Antibody-coated latex particles to which anti-human cystatin C monoclonal antibodies a, b and d were each independently bound in small amounts, were prepared, and the formation of a particle-enhanced immunoagglutinate which was dependent on the concentration of human cystatin C and was constituted of a combination recognizing different epitopes, was confirmed.
(Preparation of Antibody-Coated Latex Particles)
To a 0.5% latex solution (30 mM Tris-HCl, pH 8.5 to 9.0) of particles having an average particle size of 0.13 μm or 0.3 μm (manufactured by Sekisui Medical Co., Ltd.), an equal amount of 0.2 mg/mL solution of each cystatin C monoclonal antibody (30 mM Tris-HCl, pH 8.5 to 9.0) was added, and the mixture was stirred for one hour at 4° C. Then, an equal amount of 1% BSA solution (30 mM Tris-HCl, pH 8.5 to 9.0) was added thereto, and the resulting mixture was stirred for 30 minutes at 4° C. The mixture was centrifuged, and the supernatant was removed. Subsequently, a precipitation obtained therefrom was resuspended in purified water to obtain an antibody-coated latex particle solution. At this time, the binding amount of the antibody relative to the total weight of the antibody-coated particles was about 3.8% by weight.
(Preparation of First Reagent)
A 30 mM CHES buffer solution (pH 8.75) containing 750 mM of potassium chloride and 1% BSA was prepared, and this was used as the first reagent.
(Preparation of Second Reagent)
Equal amounts of two kinds of antibody-coated latex particle solutions were mixed, and the mixture was diluted with a 5 mM MOPS buffer solution (pH 7.0) such that the final absorbance was 2.0 OD. This dilution was used as the second reagent. The reagent was prepared by combining the antibody-coated latex particles of a-b, a-d or b-d, which were recognized to have strong reactivity from the results of the Evaluation Example 1, such that particles having the same particle size were combined.

(Assay Method)

The first reagent and the second reagent were combined, and the formation of a particle-enhanced immunoagglutinate which was dependent on the concentration of human cystatin C was identified using a Hitachi 7170 type automatic analyzer. Specifically, 100 μL of the first reagent was added to 2.5 μL of human cystatin C solution having a concentration of 0, 0.5, 1.0, 2.0, 4.0 or 8.0 mg/L, and the mixture was warmed to 37° C. for 5 minutes. Subsequently, 100 μL of the second reagent was added thereto, and the resulting mixture was stirred. Changes in the absorbance that accompanied the formation of an agglutinate for 5 minutes after the mixing, were measured as the sensitivity at a main wavelength of 570 nm and a sub-wavelength of 800 nm.

(Results)

A reagent prepared by combining antibody a-coated latex particles and antibody b-coated latex particles was used to analyze cystatin C solutions of various concentrations, and as shown in the cystatin C concentration-sensitivity curve described in FIG. 1, it was identified that the sensitivity increases in a cystatin C concentration-dependent manner in all of the particles, and an assay can be carried out. Particles having a size of 0.13 μm (closed square) exhibited slightly low sensitivity in the lower concentration region but exhibited a satisfactory sensitivity increase in the higher concentration region. Particles having a size of 0.3 μm (open square) exhibited high sensitivity in the lower concentration region but exhibited a poor sensitivity increase in the higher concentration region. Furthermore, in a reagent prepared by combining antibody a-coated latex particles and antibody d-coated latex particles, the sensitivities in the lower concentration region of the particles having a size of 0.13 μm (closed circle) and the particles having a size of 0.3 μm (open circle) were equal, and while the particles having a size of 0.13 μm exhibited an increase in sensitivity up to the higher concentration region, a sensitivity increase was hardly recognized in the particles having a size of 0.3 μm. Therefore, it was thought that although there are particles that cannot be utilized depending on the combination, both of the combinations can be applied to the immunoagglutination assay. On the other hand, in a reagent prepared by combining antibody b-coated latex particles and antibody d-coated latex particles, which are indicated by broken lines, cystatin C concentration-dependent increases in sensitivity were hardly recognized in both the particles having a size of 0.13 μm (closed triangle) and the particles having a size of 0.3 μm (open triangle), and it was thought that use of these reagents in a particle-enhanced immunoassay method was difficult.

Evaluation Example 3

Determination of the Dissociation Constant of Anti-Human Cystatin C Monoclonal Antibody by BIACORE The dissociation constants of purified anti-human cystatin C monoclonal antibodies a, b and d were calculated according to a conventional method using a BIACORE apparatus (GE Healthcare Corp.). Specifically, the anti-human cystatin C monoclonal antibodies were respectively immobilized on sensor chips using a Mouse Antibody Capture Kit (GE Healthcare Corp.), and the dissociation constants were calculated from their reactivity with human cystatin C (R&D Systems, Inc.) at concentrations of 0 μg/mL and up to 0.0625, 0.125, 0.25, 0.5, and 1.0 μg/mL (Table 2). The combinations a-b and a-d, which were considered to be applicable to particle-enhanced immunoassays in Evaluation Example 2, were such that an anti-human cystatin C monoclonal antibody a having high affinity (dissociation constant: 0.29 nM) and an anti-human cystatin C monoclonal antibody b (dissociation constant: 1.32 nM) or d (dissociation constant: 2.30 nM) having ordinary affinity were combined. Thus, the ratio of dissociation constants about 4.6 for the ratio b/a (1.32/0.29) and about 7.9 for the ratio d/a (2.30/0.29) showed clear differences in affinity between the antibodies combined. On the other hand, the combination b-d which was considered to be inapplicable to particle-enhanced immunoagglutination, was a combination of antibodies having ordinary affinity, and the ratio of dissociation constants was about 1.7 for d/b (2.30/1.32), by which a clear difference in affinity was not recognized. Thus, Hybridoma 75202 that produces the monoclonal antibody a, which is considered to have the high affinity and the highest general-purpose applicability among these antibodies, was selected. This hybridoma was deposited with International Patent Organism Depositary, National Institute of Advanced Industrial Science and Technology (305-8566, Tsukuba Central 6, 1-1-1 Higashi, Tsukuba, Ibaraki, Japan) on Nov. 20, 2008, under the Accession Number FERM BP-11186.

TABLE 2

| Antibody | Dissociation constant, KD value (nM) |
|---|---|
| a | 0.29 |
| b | 1.32 |
| d | 2.30 |

Evaluation Example 4

Examination of Anti-Human Cystatin C Monoclonal Antibody Specificity According to ELISA An evaluation of the specificities of the anti-human cystatin C monoclonal antibodies a, b and d produced in this study was carried out by ELISA. Specifically, 50 μL of PBS containing 1 μg/mL of human cystatin C and members of the cystatin family, such as human cystatin A, cystatin B, cystatin D, cystatin E/M, cystatin F, cystatin S, cystatin SA and kininogen (all by R&D Systems, Inc.), was dispensed on a 96-well microplate, and the microplate was left to stand overnight at 4° C. to immobilize the cystatins on the plate. Subsequently, this 96-well microplate was washed three times with 300 μL of PBS containing 0.05% TWEEN 20, and then a PBS containing 0.05% TWEEN 20 and 1% BSA was added to the microplate in an amount of 300 μL/well. The microplate was left to stand for 1 hour at room temperature. Thereafter, a PBS containing 1 μg/mL of each of the anti-human cystatin C monoclonal antibodies produced was added to the microplate in an amount of 50 μL/well, and the microplate was left to stand for 1 hour at room temperature. The microplate was washed three times with a PBS containing 0.05% TWEEN 20, and then a peroxidase-labeled anti-mouse antibody (Biosource, Inc.) which was diluted to 5000 times with PBS, was added to the microplate in an amount of 50 μL/well. The microplate was left to stand for 1 hour at room temperature. Thereafter, the plate was washed three times with a PBS containing 0.05% TWEEN 20, and a citrate buffer solution (pH 5) containing 0.2% ortho-phenylenediamine and 0.02% hydrogen peroxide was added to the microplate in an amount of 50 μL/well to allow a reaction to proceed for 15 minutes at room temperature. Subsequently, 4.5 N sulfuric acid was added thereto in an amount of 50 μL/well to stop the reaction, and the absorbance of each well at a wavelength of 492 nm was measured.

As controls, an anti-human cystatin C rabbit polyclonal antibody (BioVendor, Inc.) was used in place of the anti-human cystatin C monoclonal antibody, and a peroxidase-labeled anti-rabbit antibody (Cappel, Inc.) was used in place of the peroxidase-labeled anti-mouse antibody, to compare specificity.

Figure 2:
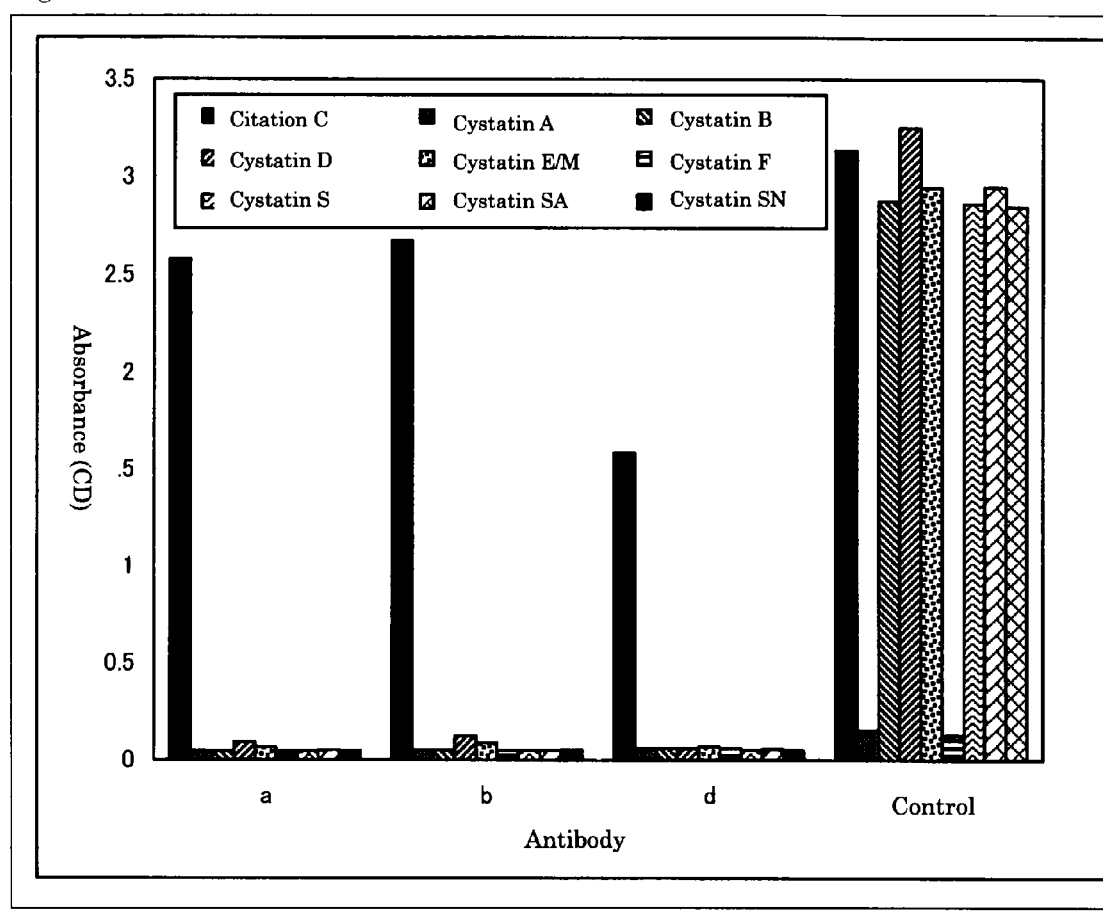
FIG. 2 is a graph showing the specificity of an anti-human cystatin C monoclonal antibody identified by ELISA, and of an anti-human cystatin C polyclonal antibody as a reference.

As shown in FIG. 2, it was confirmed that any of the monoclonal antibodies a, b and d specifically reacted only with human cystatin C. Thus, it is contemplated that cystatin C in a human body fluid can be specifically measured by using these antibodies. On the other hand, the polyclonal antibody used as a control exhibited strong reactivity toward cystatin B, cystatin D, cystatin E/M, cystatin S, cystatin SA and cystatin SN, in addition to cystatin C, to an equal extent, and also exhibited weak reactivity toward cystatin A, cystatin F and kininogen. Therefore, it was expected that in an assay using an anti-cystatin C polyclonal antibody, accurate measurement of cystatin C is impossible in a sample in which these cystatin family molecules are co-present.

The same scheme of Evaluation Examples 1 to 4 were repeated, and as a result, combinations 1 and 2 that use anti-human cystatin C monoclonal antibodies e, f and g, which are believed to be applicable to particle-enhanced immunoassays, were further discovered. These combinations were all combinations including at least one kind of high-affinity antibody having a dissociation constant of less than 1 nM. Combination 1 was a combination of high-affinity antibodies, and the ratio of dissociation constants was about 2.1. Combination 2 was a combination of a high-affinity antibody and an antibody having ordinary affinity, and the ratio of dissociation constants was about 15.4 (Table 3).

TABLE 3

| Combination | Antibody | Dissociation constant | |
| --- | --- | --- | --- |
| | | KD value (nM) | Ratio |
| 1 | a | 0.29 | 2.07 |
| | e | 0.14 | (a/e) |
| 2 | f | 0.54 | 15.37 |
| | g | 8.30 | (g/f) |

Example

A reagent for cystatin C assay of the present invention, in which the latex particle size and other general conditions were optimized for the analysis by a Hitachi 7170 type automatic analyzer, was prepared using the anti-human cystatin C monoclonal antibodies a and b, and a comparison was made on the performance with an existing cystatin C assay reagent (N-Latex Cystatin C Kit manufactured by Dade Behring, Inc.), which uses an anti-cystatin C polyclonal antibody. However, an assay reagent for general-purpose automatic analyzers that use anti-human cystatin C monoclonal antibodies, was not available.

(Preparation of Antibody-Coated Latex Particles)

To a 0.5% latex solution (30 mM Tris-HCl, pH 8.5) of particles having an average particle size of 0.15 μm, an equal amount of 0.15 mg/mL solution of antibody a or b (30 mM Tris-HCl, pH 8.5) was added, and the mixture was stirred for one hour at 4° C. Subsequently, an equal amount of 1% BSA solution (30 mM Tris-HCl, pH 8.5) was added thereto, and the resulting mixture was stirred for 30 minutes at 4° C. The mixture was centrifuged, the supernatant was removed, and then a precipitate produced therefrom was resuspended in purified water. The resultant was used as an anti-human cystatin C monoclonal antibody a- or b-coated latex particle solution. At this time, the binding amount of the antibody relative to the total weight of the antibody-coated particles was about 2.9% by weight.

(Preparation of the First Reagent)

A 30 mM Tris-HCl solution at pH 8.0 containing 750 mM of potassium chloride and 1% BSA was prepared, and this solution was used as the first reagent.

(Preparation of the Second Reagent)

Equal amounts of the antibody a-coated latex particle solution and the antibody b-coated latex particle solution were mixed, and the mixture was diluted with a 5 mM MOPS buffer solution (pH 7.0) such that the final absorbance was 1.5 OD. This dilution was used as the second reagent.

(Assay Sample)

Human serum specimen (Assay Conditions)

Hitachi 7170 Automatic Analyzer: Parameter conditions

Specimen-First reagent-Second reagent: 2.4 μL-120 μL-120 μL

Analysis method: Two-point end method (measurement point 18-34)

Measurement wavelength: Main wavelength 570 nm/sub-wavelength 800 nm

Calibration: Spline (Assay Method)

A calibration curve was produced from the measured sensitivities of human cystatin C solutions at concentrations of 0, 0.5, 1.0, 2.0, 4.0 and 10.0 mg/L, and the cystatin C concentrations in various samples were measured based on the calibration curve. Thus, correlation between samples of the present invention and reference reagents was determined (number of samples, N=50); and samples of the present invention and reference reagents were compared on simultaneous reproducibility (number of measurements in succession, n=10) and the detection limit concentration (the concentration at which the error bars of the average measured sensitivity +2SD of a sample with a zero cystatin C concentration and the average measured sensitivity −2SD of a sample with a known cystatin C concentration do not overlap, is defined as the detection limit concentration).

(Reference Reagent and Analyzer)

Reference reagent: N-Latex Cystatin C Kit

Analyzer: BN Prospec

All manufactured by Dade Behring, Inc.

(Results)

Figure 3:
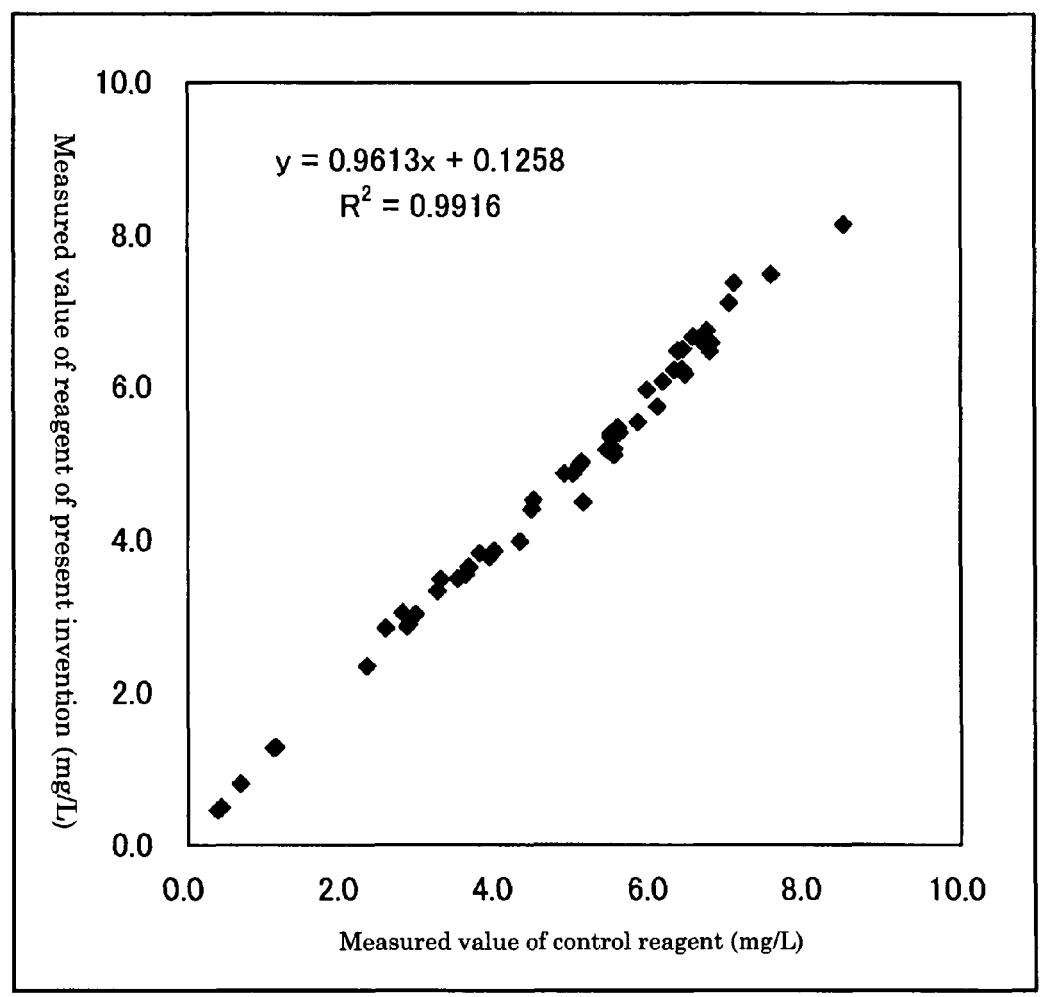
FIG. 3 is a correlation diagram (sample number N=50) for cystatin C assays between the invented reagent and the reference reagent.
Figure 4:
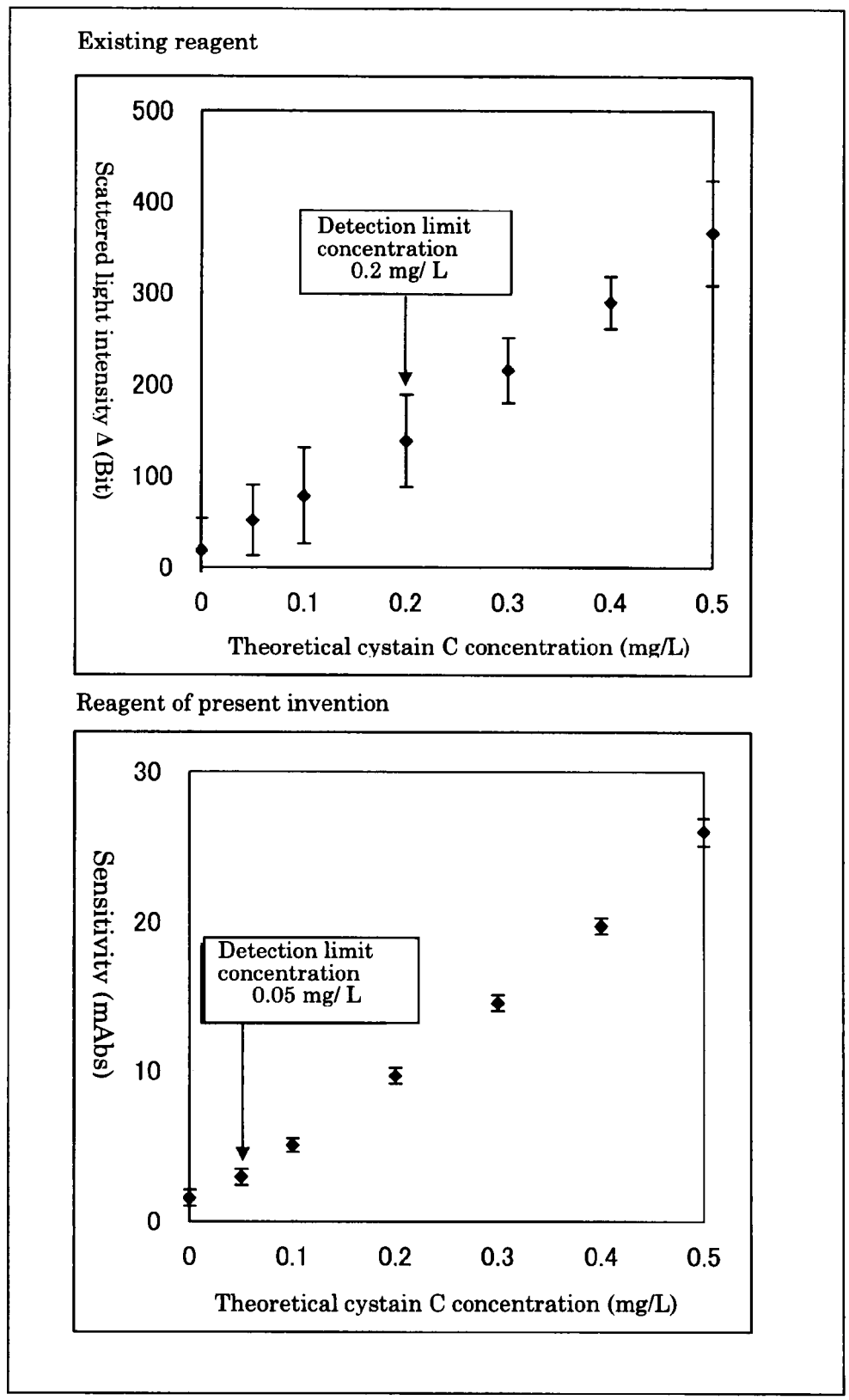
FIG. 4 is a graph showing the detection limit concentrations of the invented reagent and the reference reagent.

The correlation on the assay values between the reagent of the present invention and the reference reagent was satisfactory (FIG. 3). Furthermore, in regard to reproducibility, the coefficient of variation of the reagent of the present invention was as small as ⅕ or less of the value of existing reagents, and reproducibility was excellent (Table 4). In regard to the detection limit concentration, the detection limit concentration for cystatin C was 0.2 mg/L with the reference reagent, while 0.05 mg/L with the reagent of the present invention. Thus, it was confirmed that the reagent of the present invention was capable of detecting a concentration as low as ¼ or less of the detection limit concentration of the reference reagent (FIG. 4).

The particle-enhanced immunoassay method of the present invention which uses antibody-coated particles in which some insoluble carrier particles are coated with an anti-human cystatin C monoclonal antibodies of one type which have high affinity, and in which some insoluble carrier particles are coated with anti-human cystatin C monoclonal antibodies of another type which recognize an epitope different from that the monoclonal antibodies of the first-mentioned type recognize and which have relatively low affinity, has made it possible to establish a method for measuring cystatin C in a human body fluid, which method is inexpensive but of high performance and high specificity, and in which the binding amount of the antibody relative to the total weight of the antibody-coated particles is smaller than the binding amount that has been used in conventional reagents, i.e. from greater than 5% by weight to not less than 35% by weight.

TABLE 4

|  | Reagent of present invention | | Reference reagent | |
| --- | --- | --- | --- | --- |
|  | Sample 1 | Sample 2 | Sample 1 | Sample 2 |
|  | 0.49 | 1.99 | 0.379 | 1.64 |
|  | 0.49 | 2.00 | 0.379 | 1.69 |
|  | 0.49 | 2.01 | 0.401 | 1.66 |
|  | 0.49 | 2.01 | 0.406 | 1.64 |
|  | 0.48 | 2.01 | 0.424 | 1.75 |
|  | 0.48 | 2.01 | 0.408 | 1.71 |
|  | 0.49 | 2.01 | 0.379 | 1.75 |
|  | 0.48 | 2.01 | 0.447 | 1.75 |
|  | 0.49 | 2.01 | 0.428 | 1.71 |
|  | 0.50 | 1.99 | 0.383 | 1.72 |
| Average value (mg/L) | 0.49 | 2.01 | 0.41 | 1.70 |
| Standard deviation | 0.006 | 0.008 | 0.023 | 0.043 |
| Coefficient of variation (%) | 1.30 | 0.42 | 5.57 | 2.25 |

INDUSTRIAL APPLICABILITY

The particle-enhanced immunoassay method, reagent and kit of the present invention provide a high-performance, inexpensive, and convenient method for detecting and measuring human cystatin C in a human body fluid.

The invention claimed is:

1. A method for measuring cystatin C in a human body fluid, comprising:
(1) contacting a human body fluid with (a) first insoluble carrier particles coated with a first anti-human cystatin C monoclonal antibody which has affinity for cystatin C and (b) second insoluble carrier particles coated with a second anti-human cystatin C monoclonal antibody which has affinity for cystatin C,
wherein
the first anti-human cystatin C monoclonal antibody has an affinity for cystatin C that is higher than the second anti-human cystatin C monoclonal antibody,
the first anti-human cystatin C monoclonal antibody has a dissociation constant of less than 1 nM,
the second anti-human cystatin C monoclonal antibody on the second insoluble carrier particles recognizes an epitope of cystatin C that is different from the epitope recognized by the first anti-human cystatin C monoclonal antibody on the first insoluble carrier particles,
wherein the dissociation constant of the second anti-human cystatin C monoclonal antibody divided by the dissociation constant of the first anti-human cystatin C monoclonal antibody is two or greater,
the first insoluble carrier particles are coated with from 1% to less than 4% by weight of the first anti-human cystatin C monoclonal antibody, and
the second insoluble carrier particles are coated with from 1% to less than 4% weight of the second anti-human cystatin C monoclonal antibody,
(2) measuring the amount of cystatin C bound to the first insoluble carrier particles and the second insoluble carrier particles, and
(3) correlating the amount of cystatin C bound to the first insoluble carrier particles and the second insoluble carrier particles with the amount of cystatin C in the human body fluid.

2. The method of claim 1, wherein the average particle size of the first insoluble carrier particles is 0.1 to 0.4 μm and the average particle size of the second insoluble carrier particles is 0.1 to 0.4 μm.

3. The method of claim 1, wherein the average particle size of the first insoluble carrier particles is 0.05 to 0.5 μm and the average particle size of the second insoluble carrier particles is 0.05 to 0.5 μm.

4. The method of claim 1, wherein the average particle size of the first insoluble carrier particles is 0.1 to 0.2 μm and the average particle size of the second insoluble carrier particles is 0.1 to 0.2 μm.

5. The method of claim 1, wherein the first anti-human cystatin C monoclonal antibody is an antibody fragment containing a functional site, or a recombinant antibody and wherein the second anti-human cystatin C monoclonal antibody is an antibody fragment containing a functional site, or a recombinant antibody.

6. The method of claim 1, wherein the dissociation constant of the first anti-human cystatin C monoclonal antibody is less than 0.5 nM.

7. The method of claim 1, wherein the human body fluid is selected from the group consisting of blood serum, blood plasma, synovial fluid, milk, saliva, cerebrospinal fluid, seminal plasma, amniotic fluid, urine, and lacrimal fluid.

8. A particle-enhanced immunoassay reagent for cystatin C in a human body fluid, comprising:
(a) first insoluble carrier particles coated with a first anti-human cystatin C monoclonal antibody which has affinity for cystatin C and
(b) second insoluble carrier particles coated with a second anti-human cystatin C monoclonal antibody which has affinity for cystatin C,
wherein
the first anti-human cystatin C monoclonal antibody has an affinity for cystatin C that is higher than the second anti-human cystatin C monoclonal antibody,
the first anti-human cystatin C monoclonal antibody has a dissociation constant of less than 1 nM,
the second anti-human cystatin C monoclonal antibody on the second insoluble carrier particles recognizes an epitope of cystatin C that is different from the epitope recognized by the first anti-human cystatin C monoclonal antibody on the first insoluble carrier particles,
wherein the dissociation constant of the second anti-human cystatin C monoclonal antibody divided by the dissociation constant of the first anti-human cystatin C monoclonal antibody is two or greater,
the first insoluble carrier particles are coated with from 1% to less than 4% by weight of the first anti-human cystatin C monoclonal antibody, and the second insoluble carrier particles are coated with from 1% to less than 4% weight of the second anti-human cystatin C monoclonal antibody.

9. The reagent of claim 8, wherein the average particle size of the first insoluble carrier particles is 0.1 to 0.4 μm and the average particle size of the second insoluble carrier particles is 0.1 to 0.4 μm.

10. The reagent of claim 8, wherein the average particle size of the first insoluble carrier particles is 0.05 to 0.5 μm and the average particle size of the second insoluble carrier particles is 0.05 to 0.5 μm.

11. The reagent of claim 8, wherein the average particle size of the first insoluble carrier particles is 0.1 to 0.2 μm and the average particle size of the second insoluble carrier particles is 0.1 to 0.2 μm.

12. The reagent of claim 8, wherein the first anti-human cystatin C monoclonal antibody is an antibody fragment containing a functional site, or a recombinant antibody and wherein the second anti-human cystatin C monoclonal antibody is an antibody fragment containing a functional site, or a recombinant antibody.

13. The reagent of claim 8, wherein the dissociation constant of the first anti-human cystatin C monoclonal antibody is less than 0.5 nM.

14. The method of claim 1, wherein the correlating is accomplished using a calibration curve produced from measured sensitivities of human cystatin C solutions.

* * * * *